(12) United States Patent
Schonholz et al.

(10) Patent No.: US 10,201,688 B2
(45) Date of Patent: Feb. 12, 2019

(54) BIOPSY SPACER DEVICE AND METHOD OF OPERATION

(71) Applicants: Steven Michael Schonholz, Warren, MA (US); Robert T. T. Gettens, Longmeadow, MA (US); Zachary Coopee, Hampden, MA (US); Dena Navarroli, West Hartford, CT (US)

(72) Inventors: Steven Michael Schonholz, Warren, MA (US); Robert T. T. Gettens, Longmeadow, MA (US); Zachary Coopee, Hampden, MA (US); Dena Navarroli, West Hartford, CT (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 351 days.

(21) Appl. No.: 14/992,383

(22) Filed: Jan. 11, 2016

(65) Prior Publication Data

US 2016/0121089 A1    May 5, 2016

Related U.S. Application Data

(63) Continuation-in-part of application No. 14/594,619, filed on Jan. 12, 2015, now Pat. No. 9,233,231, which
(Continued)

(51) Int. Cl.
*A61M 29/00* (2006.01)
*A61M 29/02* (2006.01)
(Continued)

(52) U.S. Cl.
CPC ......... *A61M 29/02* (2013.01); *A61B 10/0041* (2013.01); *A61B 10/02* (2013.01);
(Continued)

(58) Field of Classification Search
CPC .......... A61N 5/1015; A61N 2005/1003; A61N 5/1002; A61N 2005/1023; A61N 5/1007;
(Continued)

(56) References Cited

U.S. PATENT DOCUMENTS 5,913,813 A    6/1999  Williams et al.
6,036,631 A    3/2000  McGrath et al.
(Continued)

FOREIGN PATENT DOCUMENTS

EP       1618924      1/2006
WO       02092162     11/2002
(Continued)

*Primary Examiner* — Jason E Flick
(74) *Attorney, Agent, or Firm* — Cantor Colburn LLP

(57) ABSTRACT

A breast cavity spacer device, a kit for performing a biopsy and a method of performing a biopsy, such as for use with a percutaneous lumpectomy, is provided. The breast cavity spacer device includes a catheter. A self-sealing balloon member is removably and fluidly coupled on one end of the catheter. An umbrella valve is coupled to the catheter adjacent the balloon member, the umbrella valve being configured to fluid flow into the balloon in response to fluid flow from an end of the catheter opposite the balloon and prevent fluid flow from the balloon when fluid flow from the end of the catheter is stopped.

11 Claims, 16 Drawing Sheets

Related U.S. Application Data is a continuation of application No. 13/416,459, filed on Mar. 9, 2012, now Pat. No. 8,932,251.

(60) Provisional application No. 61/451,187, filed on Mar. 10, 2011.

(51) Int. Cl.
| | |
|---|---|
| *A61B 10/04* | (2006.01) |
| *A61N 5/10* | (2006.01) |
| *A61B 10/02* | (2006.01) |
| *A61B 17/02* | (2006.01) |
| *A61B 10/00* | (2006.01) |
| *A61B 90/00* | (2016.01) |
| *A61M 39/24* | (2006.01) |
| *A61M 27/00* | (2006.01) |
| *A61M 25/10* | (2013.01) |
| *A61B 50/30* | (2016.01) |
| *A61B 17/00* | (2006.01) |

(52) U.S. Cl.
CPC .......... *A61B 10/0233* (2013.01); *A61B 10/04* (2013.01); *A61B 17/0218* (2013.01); *A61B 90/02* (2016.02); *A61N 5/1015* (2013.01); *A61B 50/30* (2016.02); *A61B 2017/00557* (2013.01); *A61B 2017/0225* (2013.01); *A61M 27/00* (2013.01); *A61M 2025/1054* (2013.01); *A61M 2025/1086* (2013.01); *A61M 2039/2466* (2013.01); *A61M 2210/1007* (2013.01)

(58) Field of Classification Search
CPC ......... A61N 5/1014; A61N 2005/1018; A61M 25/1002; A61M 25/10; A61M 31/00; A61M 37/0069; A61M 2025/105; A61M 2025/1054; A61M 2025/0039; A61M 2025/004; A61M 2025/0004; A61B 2017/22051; A61B 17/12136; A61B 17/3415; A61B 17/3468; A61K 51/1282
USPC ...................................................... 604/96.01
See application file for complete search history.

(56) References Cited

U.S. PATENT DOCUMENTS

| | | | |
|---|---|---|---|
| 6,117,064 A | 9/2000 | Apple et al. | |
| 6,149,575 A | 11/2000 | Leonhardt | |
| 6,312,405 B1 * | 11/2001 | Meyer | A61B 17/12099 |
| | | | 206/363 |
| 6,413,204 B1 | 7/2002 | Winkler et al. | |
| 7,056,274 B2 | 6/2006 | Apple et al. | |
| 7,404,791 B2 | 7/2008 | Linares et al. | |
| 7,749,150 B2 | 7/2010 | Kindlein et al. | |
| 2012/0088952 A1 | 4/2012 | Lubock et al. | |
| 2014/0196721 A1 * | 7/2014 | Gilhuly | A61M 16/209 |
| | | | 128/207.15 |

FOREIGN PATENT DOCUMENTS

| | | |
|---|---|---|
| WO | 02102458 | 12/2002 |
| WO | 2004043531 | 5/2004 |
| WO | 2006041733 | 4/2006 |
| WO | 2006065299 | 6/2006 |

\* cited by examiner

BIOPSY SPACER DEVICE AND METHOD OF OPERATION

CROSS REFERENCE TO RELATED APPLICATIONS

The present application is a continuation-in-part application of U.S. patent application Ser. No. 14/594,619 filed on Jan. 12, 2015 entitled "Biopsy Spacer Device and Method of Operation", which is a continuation application of U.S. patent application Ser. No. 13/416,459 filed on Mar. 9, 2012 entitled "Biopsy Spacer Device and Method of Operation", which claims the benefit of U.S. Provisional Application, Ser. No. 61/451,187 filed Mar. 10, 2011, the contents of all which are incorporated by reference herein.

BACKGROUND OF THE INVENTION

The subject matter disclosed herein relates to a spacer device for cavities formed during a biopsy and in particular to a spacer device for maintaining a cavity formed during a percutaneous lumpectomy open for later use during radiation therapy.

Percutaneous lumpectomy is a method shown in FIGS. 1-4 that is used by physicians to diagnose breast and treat cancer. One procedure uses a stereotactic system involving a procedure platform or table that supports the patient and maintains the patient's breast 20 in a fixed location. The system includes an x-ray imaging device and a three-dimensional positioning system. X-ray images of the breast 20 are taken at three locations relative to the axis of the table to identify the location of a tumor or area of interest 22 by the clinician. The coordinates of the tumor 22 are utilized by the three-dimensional positioning system to guide a "wand" or needle 24 to the area of interest.

The physician makes an incision location 26 and inserts the needle 24. The physician controls the progression of the needle 24 into the incision 26. Once the needle 24 is in the proper location, a device 28 on the end of the needle 24 deploys a plurality of cauterizing filaments 30 that capture the area of interest 22 and cauterize the remaining tissue. With the area of interest 22 captured, the needle 24 is removed. The removal of the area of interest 22 leaves an elliptically shaped cavity 32 and an insertion track 34 in the breast 20.

Following the biopsy procedure, there may be a period of up to four days while the specimen 22 is evaluated by a pathologist to determine if the tumor is cancerous and if it has been completely excised with clear margins. If it is determined that all of the tumor has not been removed, the physician makes a second incision to remove additional tissue. Once all of the tumor has been removed, a third incision is made for the insertion of a brachytherapy balloon that is used for radiation treatments.

While existing devices and methods of diagnosing and treating breast cancer are suitable for their intended purposes, the need for improvement remains in particular in reducing the number of incisions and in the placement of the brachytherapy balloon.

BRIEF DESCRIPTION OF THE INVENTION

According to one aspect of the invention, a breast cavity spacer device, a kit for performing a biopsy and a method of performing a biopsy, such as for use with a percutaneous lumpectomy, is provided. The breast cavity spacer device includes a catheter. A self-sealing balloon member is removably and fluidly coupled on one end of the catheter. An umbrella valve is coupled to the catheter adjacent the balloon member, the umbrella valve being configured to fluid flow into the balloon in response to fluid flow from an end of the catheter opposite the balloon and prevent fluid flow from the balloon when fluid flow from the end of the catheter is stopped.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

Figure 1:
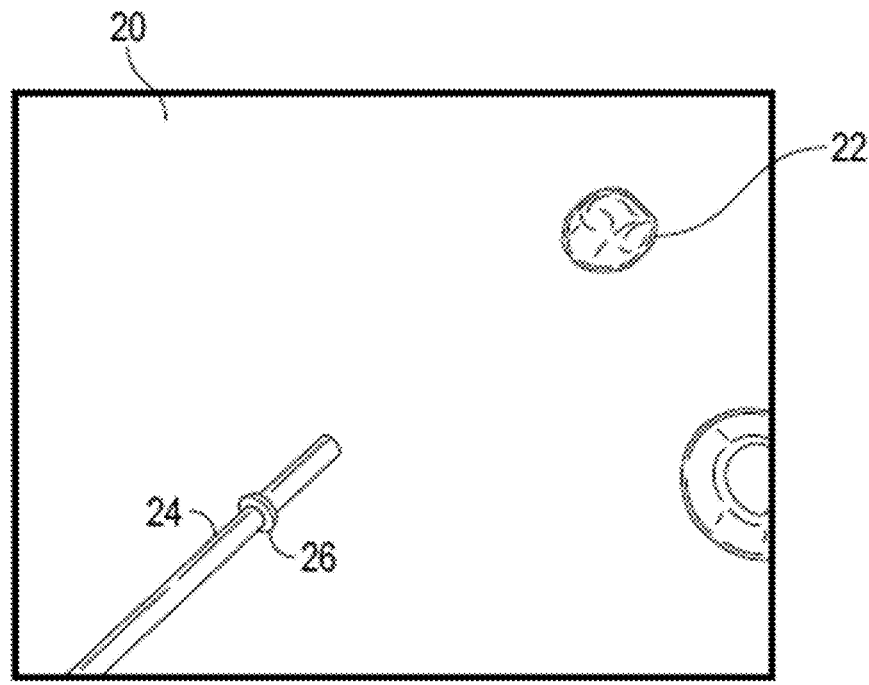
FIGS. 1-5 are illustrations of a prior art biopsy procedure.
Figure 2:
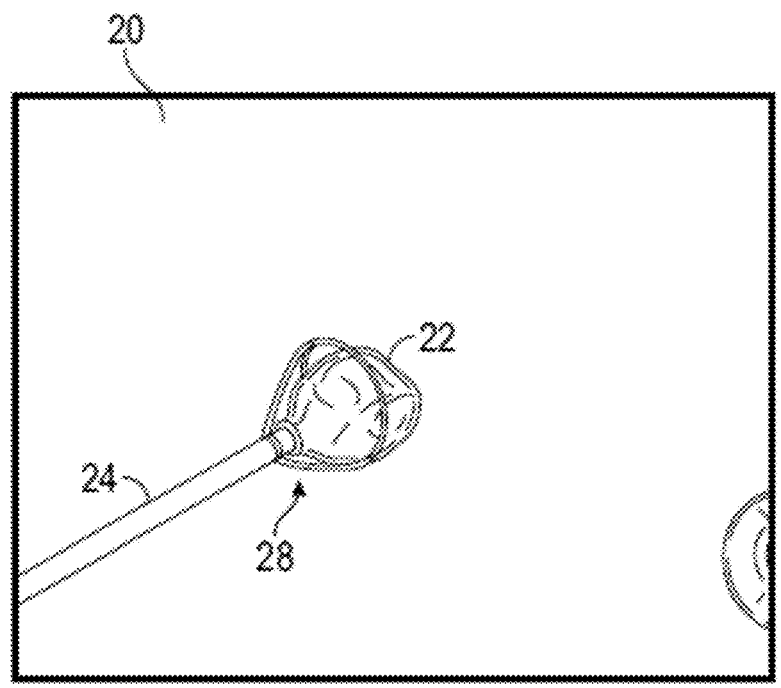
Figure 3:
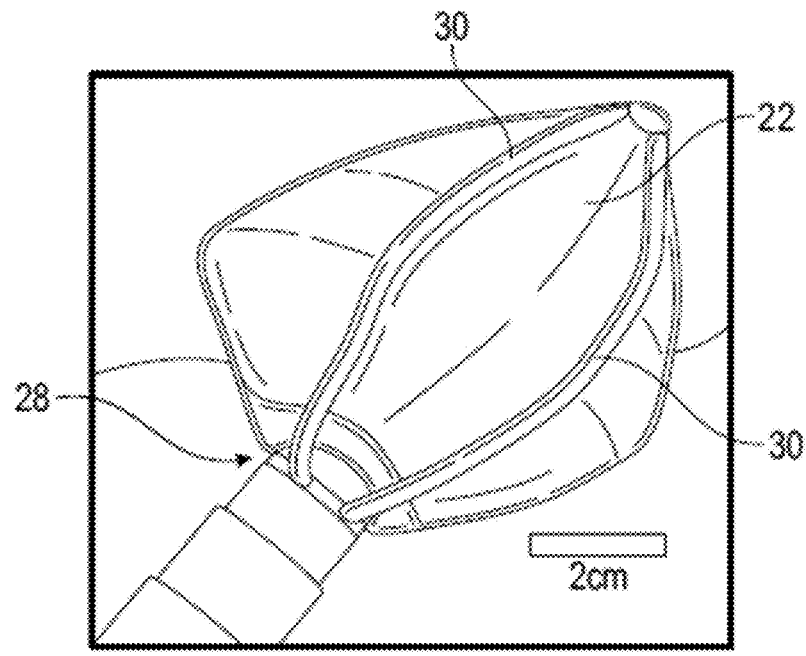
Figure 4:
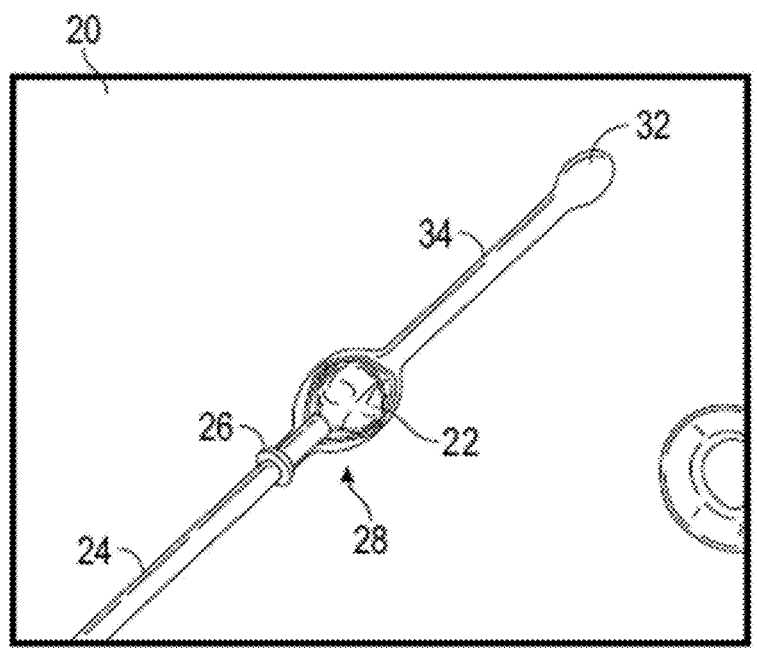
Figure 5:
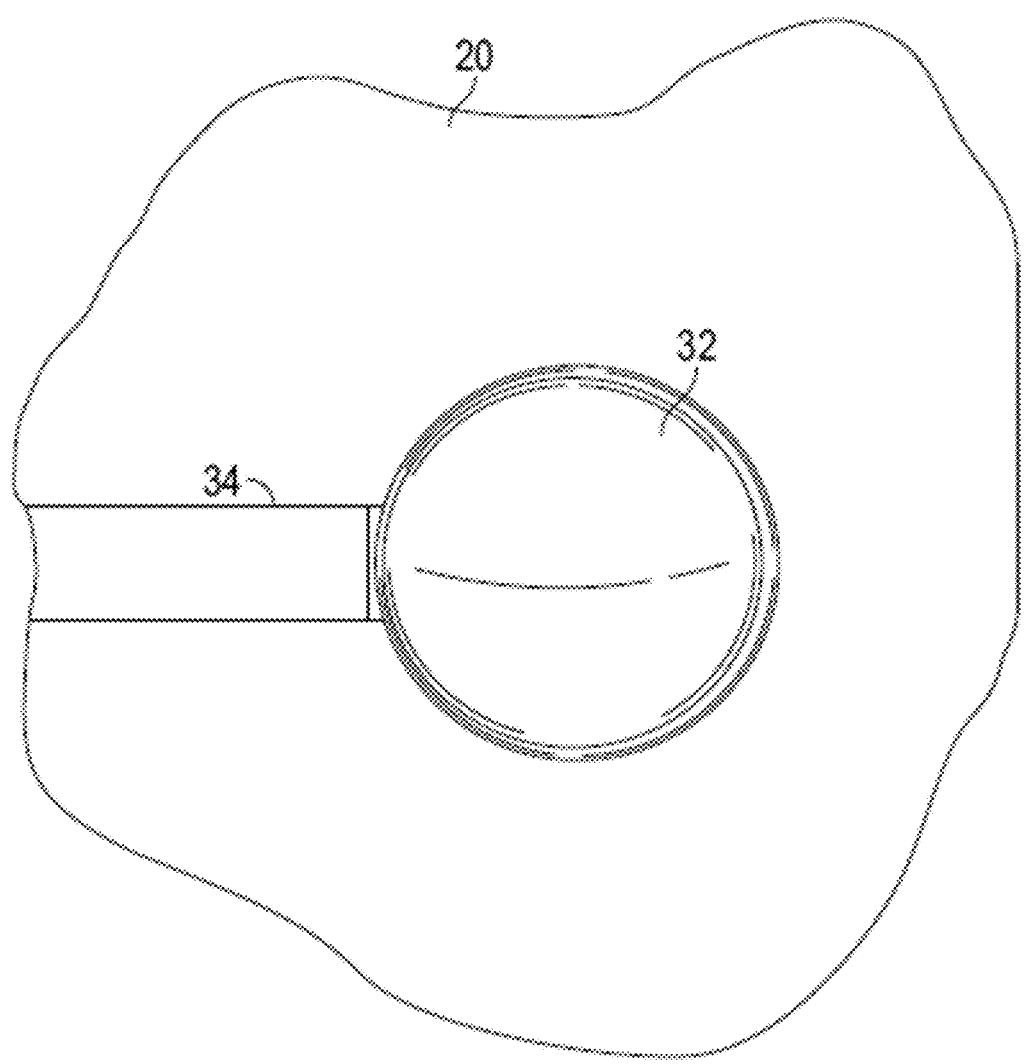
Figure 6:
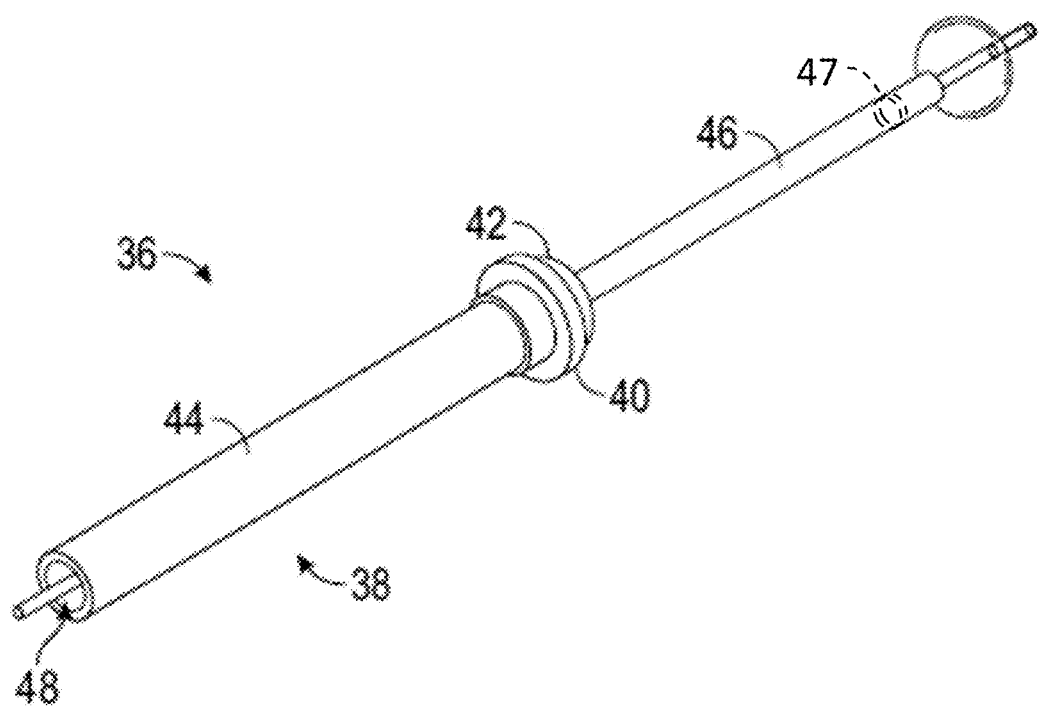
FIG. 6 is a perspective view illustration of a spacer device in accordance with an embodiment of the invention.
Figure 7:
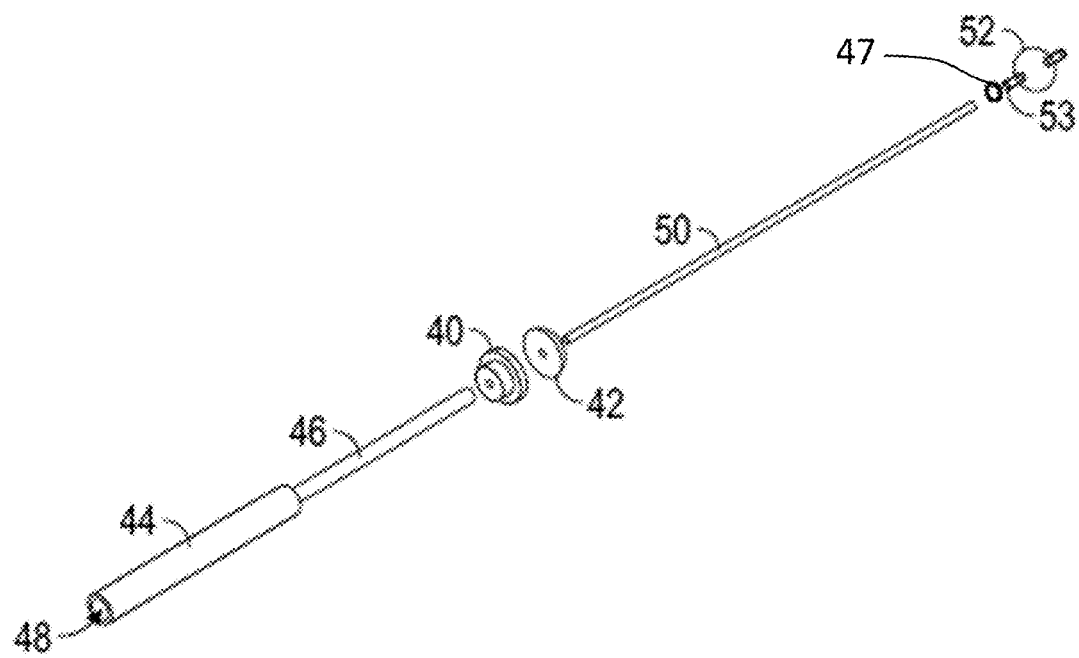
FIG. 7 is an exploded view illustration of the spacer device of FIG. 6.
Figure 8:
FIG. 8 is a side view of a catheter balloon assembly for use with the spacer device of FIG. 6.

The detailed description explains embodiments of the invention, together with advantages and features, by way of example with reference to the drawings.

DETAILED DESCRIPTION OF THE INVENTION

A percutaneous lumpectomy is a biopsy procedure that removes cancerous tissue and leaves behind an open tract. Embodiments of the present invention provide a breast cavity spacer device that is utilized after the lumpectomy procedure to keep the tract open for the three to four days while the removed tissue is analyzed. The breast cavity spacer device may provide advantages in eliminating or reducing the number of incisions needed to treat the patient. The breast cavity spacer device may provide advantages in allowing radiation treatment to be initiated quickly if the tumor is found to be cancerous. The breast cavity spacer device may provide further advantages allowing a brachytherapy balloon to be placed in substantially the same position as the removed tumor. The breast cavity spacer device may provide yet further advantages in the delivery of medication to the cavity to decrease patient pain or discomfort.

Referring to FIGS. 6-10 an exemplary embodiment of a breast cancer spacer device 36 is shown. The device 36 includes a wand member 38 having a body 44 with a projection 46 extending from one end. The wand member 38 further includes a threaded flange 40 and a holder member 42 disposed adjacent the projection 46. The wand member 38 is configured to interface with the handle of a stereotactic lesion excision system (not shown) that is used for the lumpectomy procedure. In one embodiment, the stereotactic lesion excision system is a MammoTest® Intact® Medical Breast Lesion Excision System manufactured by Siemens AG. The stereotactic system is used to guide the device 36 to the location of the removed tissue. It should be appreciated that embodiments of the device 36 may be used with any radiologic technique for visualizing tumors that may have resection, such as ultrasound for example.

A bore 48 extends longitudinally through the body 44 and projection 46. The bore 48 is sized to allow a catheter 50 to extend through the wand member 38. The wand member 38 is made from a suitable material such as high molecular weight polyethylene for example. The thread flange 40 is configured to allow the wand member 38 to be secured into the stereotactic system handle while it is being inserted into the breast 20. The holder member 42 keeps the threads in the proper location on the wand member 38 while procedure is being performed.

Figure 10:
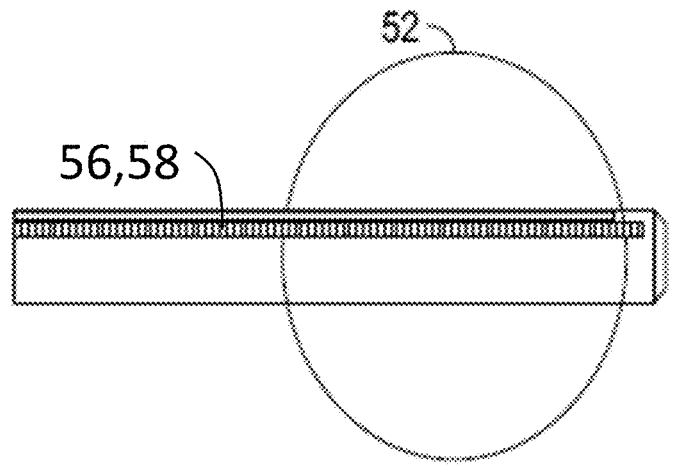
FIG. 10 is a schematic illustration of the balloon end portion of the breast cancer spacer device of FIG. 6.
Figure 11:
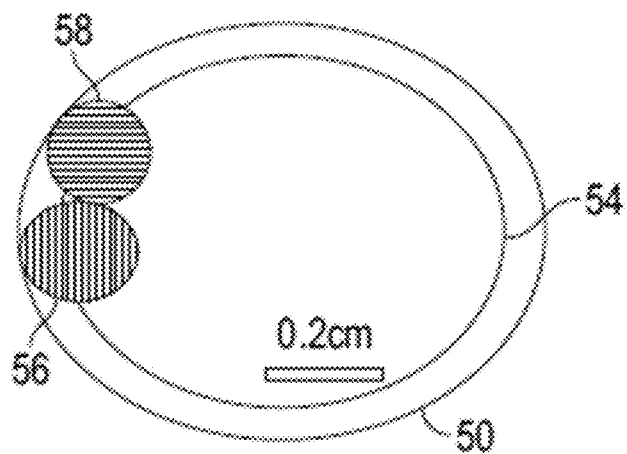
FIG. 11 is a sectional schematic illustration of the catheter portion of the spacer device of FIG. 6.

Extending through the bore 48 is a catheter 50. The catheter 50 is a generally thin walled member of sufficient length to allow the physician to extend the catheter through the bore 48 to place a balloon member 52 in substantially the same location where the tumor 22 was excised. In one embodiment, the catheter 50 includes three conduits or catheters for the delivery or extraction of materials from the patient. As shown in FIGS. 10-11, these conduits may include a drainage catheter 54, a medication catheter 56 and a balloon inflation catheter 58. It should be appreciated that this provides advantages in providing a means for inflating the balloon, in the draining of any seroma that may form and in the delivery of medication to ease pain or discomfort.

Figure 9A:
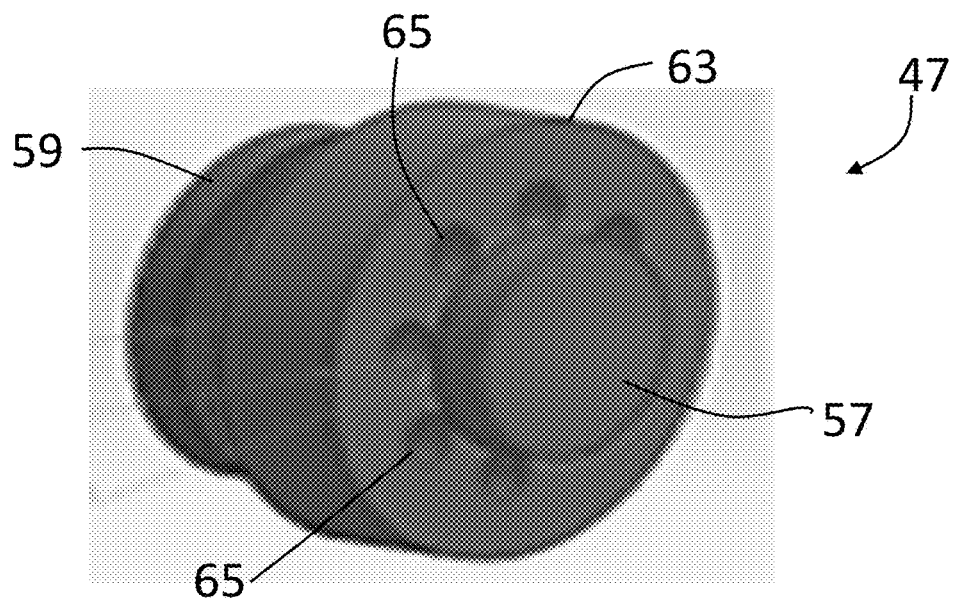
FIG. 9A and FIG. 9B are embodiments of a gate valve for use with the catheter balloon assembly of FIG. 8
Figure 9B:
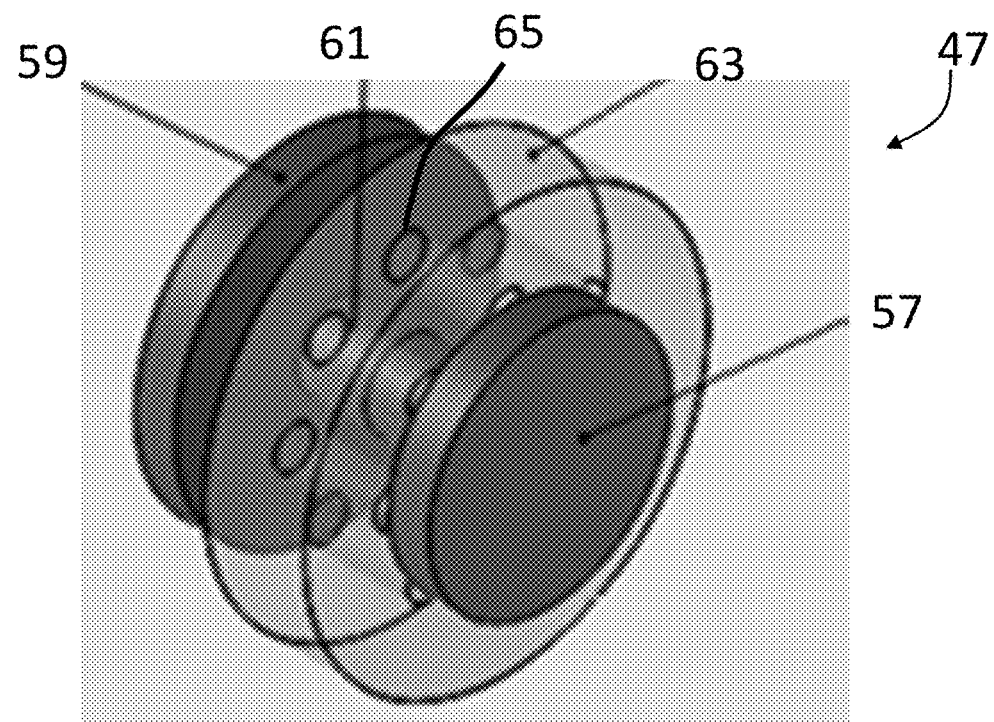

In the exemplary embodiment, the catheter 50 may include an umbrella valve 47. An embodiment of the umbrella valve 47 is shown in FIGS. 9A, 9B. The umbrella valve 47 assembly includes four different members to define a two way check valve. The valve 47 includes an end piece 57, head piece 59, rod 61, and holder member 63. In an embodiment, the holder member has a 1 centimeter in diameter. The valve 47 is imbedded within the catheter 50 before the entrance of the balloon 52. The proximal side of end piece 57 of the valve 47 may be located closest to the holder member 422 side of the catheter 50. The umbrella valve 47 operates based on pressure differentials created by injection of a liquid such as saline. When the pressure is applied to the valve 47 it opens allowing for fluid to pass and enter the balloon 52. If the pressure within the balloon 52 exceeds the pressure in the catheter 50 (infusion is stopped or the balloon 52 is full) the valve 47 will close, stopping fluid from entering or exiting the balloon.

The holder member 63 is coupled in a fixed/stationary manner within and relative to the catheter 50. In an embodiment, the diameter of the holder member 63 is 1.0 cm have a the center hole sized to allow movement of the rod 61 having a diameter of 0.20 cm. In an embodiment, the holder member 63 includes eight openings 65 evenly spaced radially about the holder member 63. The openings 65 may have a diameter of 0.10 cm and are positioned in the flow path of fluid through the valve 47. When the holes 65 are not covered by the head piece 59 they allow free flow of the fluid. In an embodiment, the holder member 63 has a width of is 0.25 cm and is positioned directly before the balloon 52 at the end of the catheter 50.

The head piece 59 is connected to the rod 61 on the balloon 50 side of the valve 47. In an embodiment, the head piece 59 has a diameter of 0.8 cm with a centrally located recess sized and shaped to receive the rod 61. In an embodiment, the recess has a diameter of 0.20 cm and is circularly shaped. In an embodiment, the head piece 59 is made from an elastomeric or rubber material. In operation, the head piece 59 is used to close the valve 47 when infusion is completed. The head piece 59 is configured to move between an open position and a closed position. In the closed position, the head piece 59 moved into contact with the holder member 63 where it blocks the holes 65 and prevents fluid flow into the balloon 52. In an embodiment, the head piece 59 has a width of is 0.1 cm.

The end piece 57 provides for mechanical drainage of fluid from the balloon 52. The end piece 57 functions to limit the rod 61 and head piece 59 from being removed from the holder member 63 while providing for opening of the valve 47 for drainage. In an embodiment, the end piece 57 has a diameter of 0.60 cm with a 0.20 cm diameter circular recess sized to receive the rod 61. As will be discussed in more detail herein, the end piece 57 cooperates with a drainage device 100 (FIG. 18) to open the valve 47. In an embodiment, the end piece 57 has a width of 0.10 cm.

The rod 61 connects the head piece 59 and end piece 57. In the exemplary embodiment, the rod 61 has a cylindrical shape with a diameter of 0.20 cm and a height of 0.50 cm. In operation, the connection of the rod 61 to the head piece 59 and end piece 57 allow components to move between open and closed position when assembled through the holder member 63.

In one embodiment, the catheter 50 may have a manifold 60 (FIG. 8) that bifurcates the catheter to allow multiple internal conduits 54, 56, 58 to be segregated for their intended functions.

The balloon member 52 is arranged on one end of the catheter 50 in fluid communication with the inflation catheter 56. Once the balloon 52 is in the desired location (e.g. the location where the tissue 22 was removed), the balloon 52 is configured to be inflated with saline solution that will keep the cavity 32 open (e.g. will not close due to healing). The balloon 52 is made from a suitable material to withstand the pressures internal to the patient's body. Once the balloon 52 is inflated, the catheter 50 and the wand member 38 are removed. In the exemplary embodiment, the balloon 52 is a self-sealing balloon that allows the catheter 50 to be removed with substantially no loss of pressure. In one embodiment, the balloon 50 includes a tube portion 53 that extends from one side. The tube portion 53 may be pinched by the physician when the catheter 50 is removed. The tube portion 53 may be positioned within the insertion tract 34 to keep the tract 34 open between the time the tissue 22 is removed and subsequent procedures are performed (e.g. 2-4 days). In one embodiment, the balloon member is elliptically shaped and available in three sizes corresponding to the three sizes of brachytherapy balloons. In another embodiment, the balloon member 52 has a water vapor transmission rate of less than 0.01 g/m$^2$/hr.

After the tissue sample 22 is analyzed, the physician will then drain the saline from the balloon member 52 and the balloon member 52 is removed from the cavity 32 and track 34. In one embodiment, the balloon 50 is deflated by draining the saline solution and applying a negative pressure within the interior of the balloon 50. With the balloon and catheter removed, the physician may then use the same incision 26 to excise additional tissue if the tumor was not completely removed, or insert a brachytherapy balloon to initiate radiation treatment. It should be appreciated that the use of the same incision reduces the pain and discomfort for the patient and allows the physician to place the brachytherapy balloon in substantially the same location as where the tumor 22 was removed.

Figure 12:
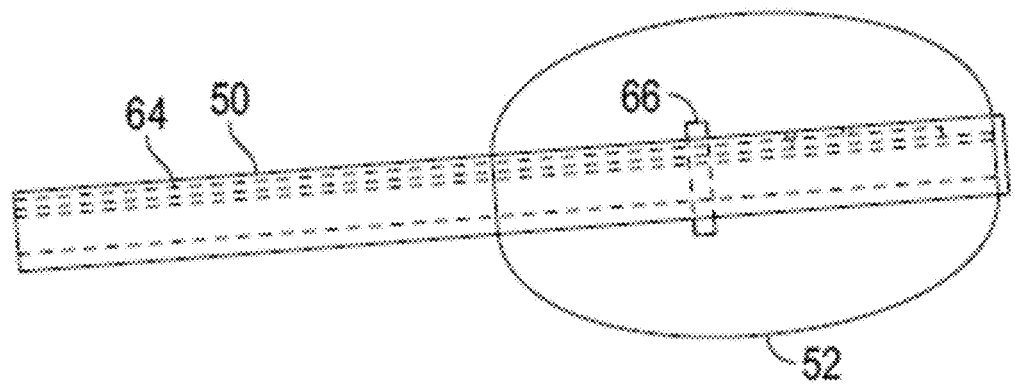
FIG. 12 is a side view of another embodiment of a spacer device
Figure 13:
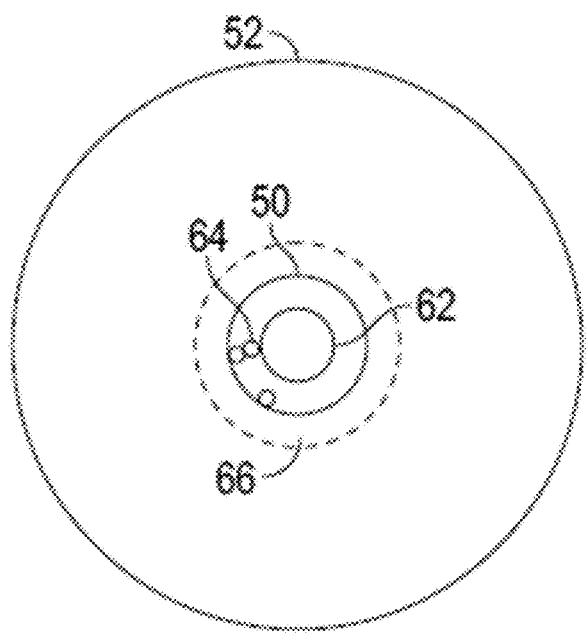
FIG. 13 is an end view of the spacer device of FIG. 11.

Another embodiment of the spacer device 36 is shown in FIGS. 12-13. In this embodiment, the catheter extends through the balloon 52. The catheter includes a first conduit 62 that includes an opening on the end of the catheter 50 to allow for drainage of seroma. The catheter further includes a second conduit 64 that is in fluid communication with a cylindrical projection 66. The cylindrical projection 66 is positioned within the interior of the balloon 52. During operation, once the balloon 52 is in the desired position, a fluid such as saline for example flows through the second conduit 64 and into the interior of the balloon 52. The fluid inflates the balloon 52 to fill the cavity. In one embodiment, the balloon 52 is made from a self-sealing type material that allows the catheter 52 to be removed after the procedure is complete while leaving the inflated balloon 52 in place.

Figure 14:
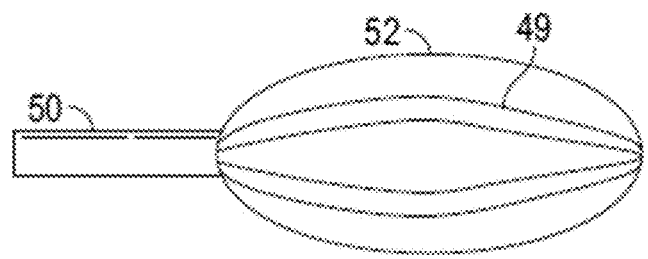
FIG. 14 is a side view of another embodiment of a spacer device.
Figure 15:
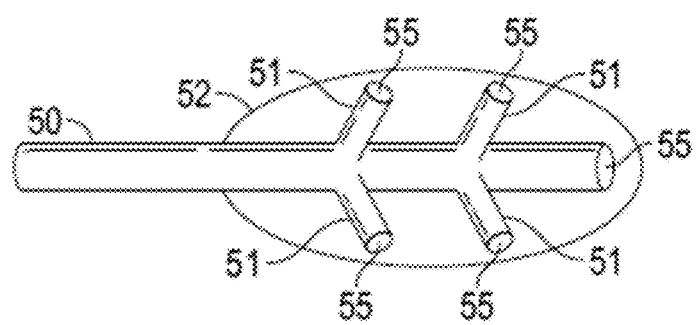
FIG. 15 is a side view of another embodiment of a spacer device.

Another embodiment for a balloon 52 is illustrated in FIG. 14. In this embodiment, the balloon 52 includes one or more ridges 49 disposed longitudinally about the periphery of the balloon 52. The ridges 49 provide additional resistance and provide advantages in preventing the balloon 52 from falling out of the cavity. Yet another embodiment for a balloon 52 and catheter 50 is shown in FIG. 15. In this embodiment, the catheter 50 has a plurality of branch conduits 51 with openings 55 on the end. The openings 55 allow seroma from areas disposed about the cavity. In one embodiment, medication may also be delivered through the openings 55.

Figure 16:
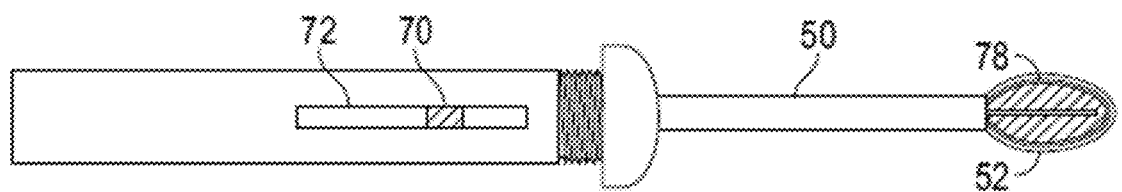
FIG. 16-17 are side views of another embodiment of a spacer device having a mechanical expansion arrangement.
Figure 17:
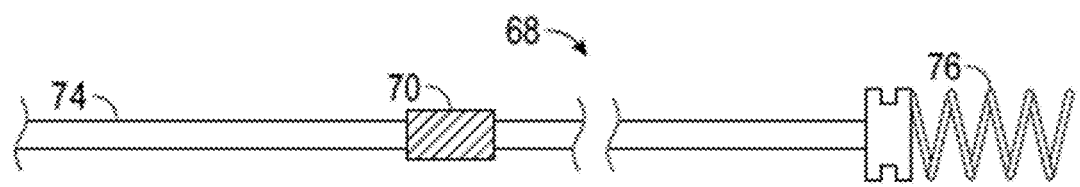

Yet another embodiment of the spacer device 36 is shown in FIGS. 16-17. In this embodiment, the spacer device 36 includes a mechanical expansion assembly 68. The assembly 68 includes a button 70 that slides within a slot 72 in the body 44. The button 70 is coupled to a shaft 74 having a spring 76. On one end of the shaft 74 are a plurality of slats 78 that are movable from a first position inside the catheter 50 to a second position inside the balloon 52. As the button 70 is slid within the slot the slats 78 move from the first position to the second position bend to the desired shape of the cavity as they exit the catheter 50.

Figure 18:
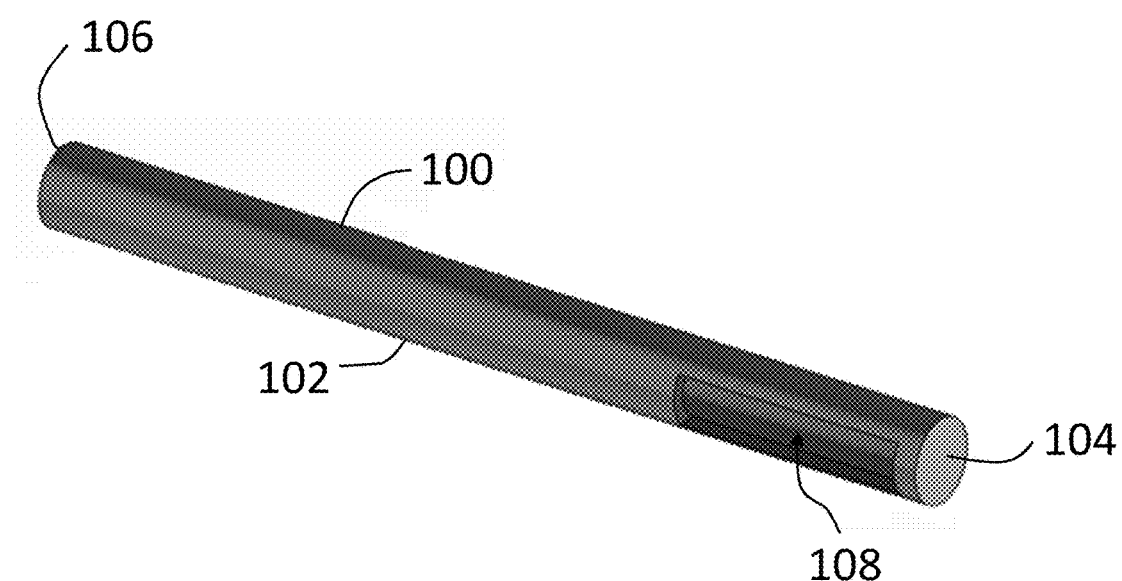
FIG. 18 is a perspective view of a draining member for use with embodiments of the spacer device.

Referring now to FIG. 18, an embodiment of a drainage device 100 is shown that is configured to cooperate with the valve 47 to allow for removal of fluid from the balloon 52 such as when the surgeon needs to re-enter the patient for example. The drain device 100 includes a cylindrical body 102 having a closed end 104 and an open end 106. The open end 106 is sized, shaped and configured to attach to a syringe 102 (FIG. 23), such as a 10 gauge syringe for example, to allow the draining device 100 to enter the catheter 50. In the exemplary embodiment, the body 102 has a diameter of 0.5 cm. The body 102 includes an internal passage that connects the open end 106 to an opening 108. In the exemplary embodiment, the opening 108 is positioned adjacent the end 104.

As will be discussed in more detail below, the insertion of the draining device 100 into the catheter 50 contacts and moves the end piece 57 breaking the pressure holding the valve 47 in a closed position. After relieving the pressure fluid may be withdrawn from the balloon 52 via the syringe 102.

Figure 19:
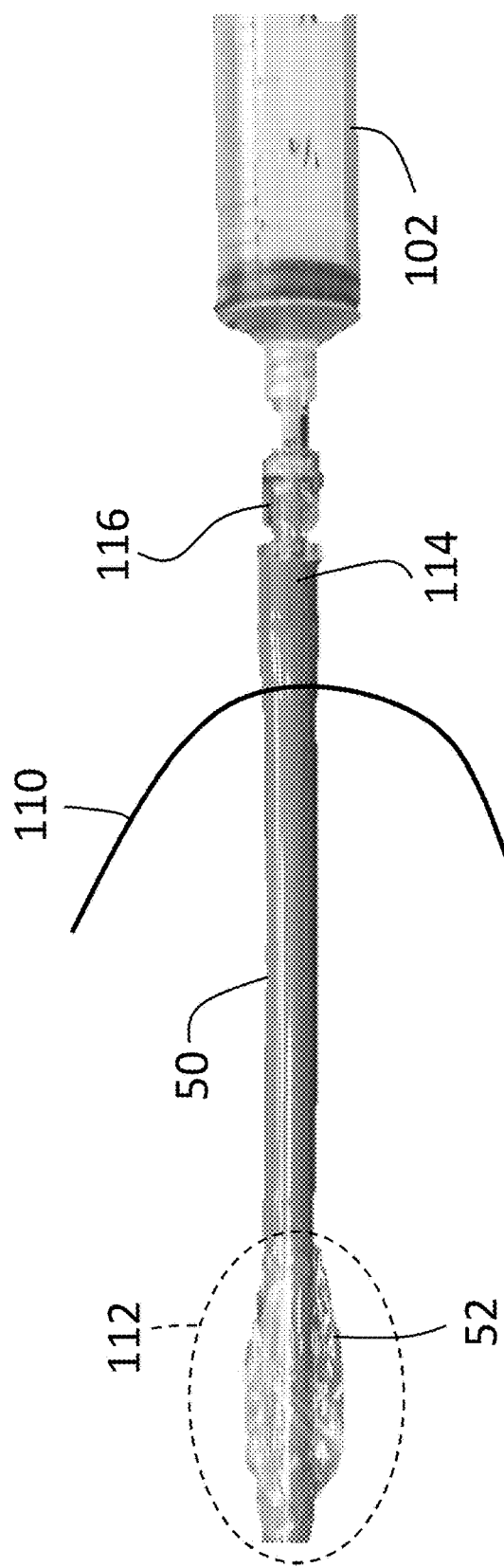
Figure 20:
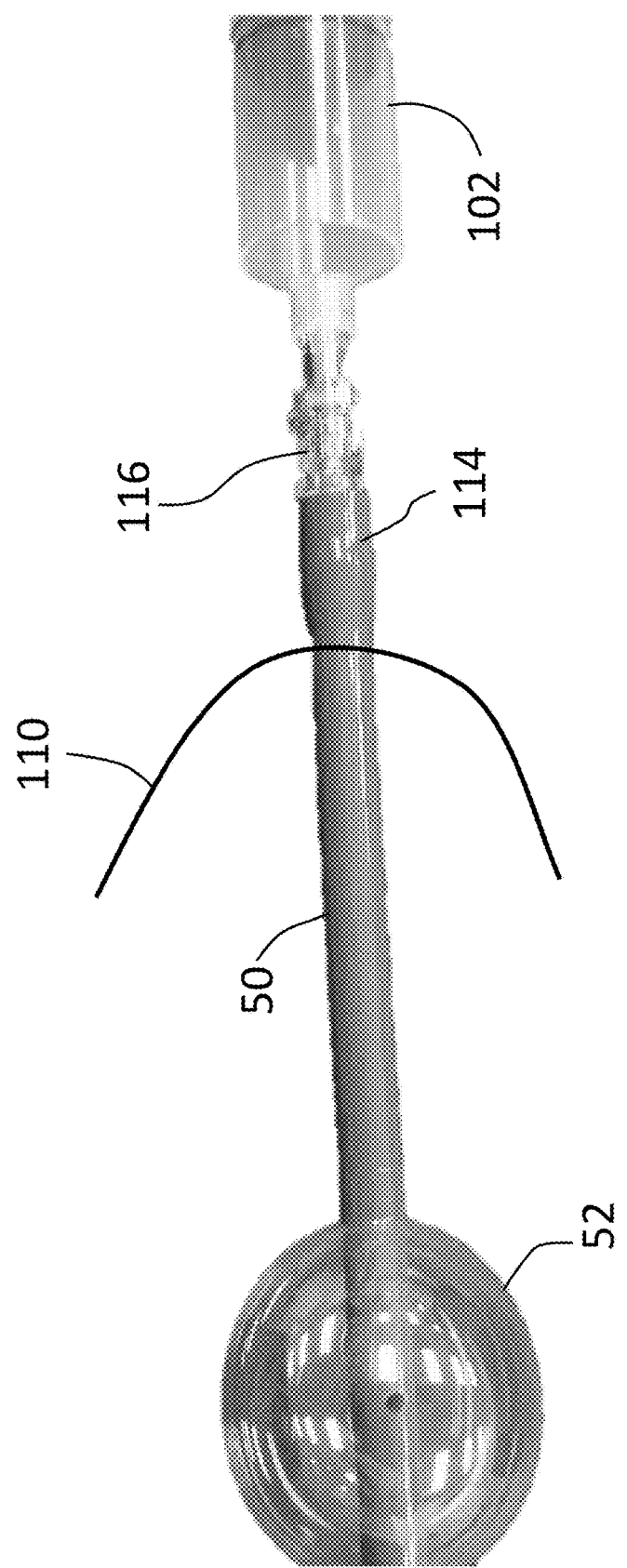
FIGS. 20-23 illustrate a method of performing a biopsy procedure in accordance with some embodiments.
Figure 21:
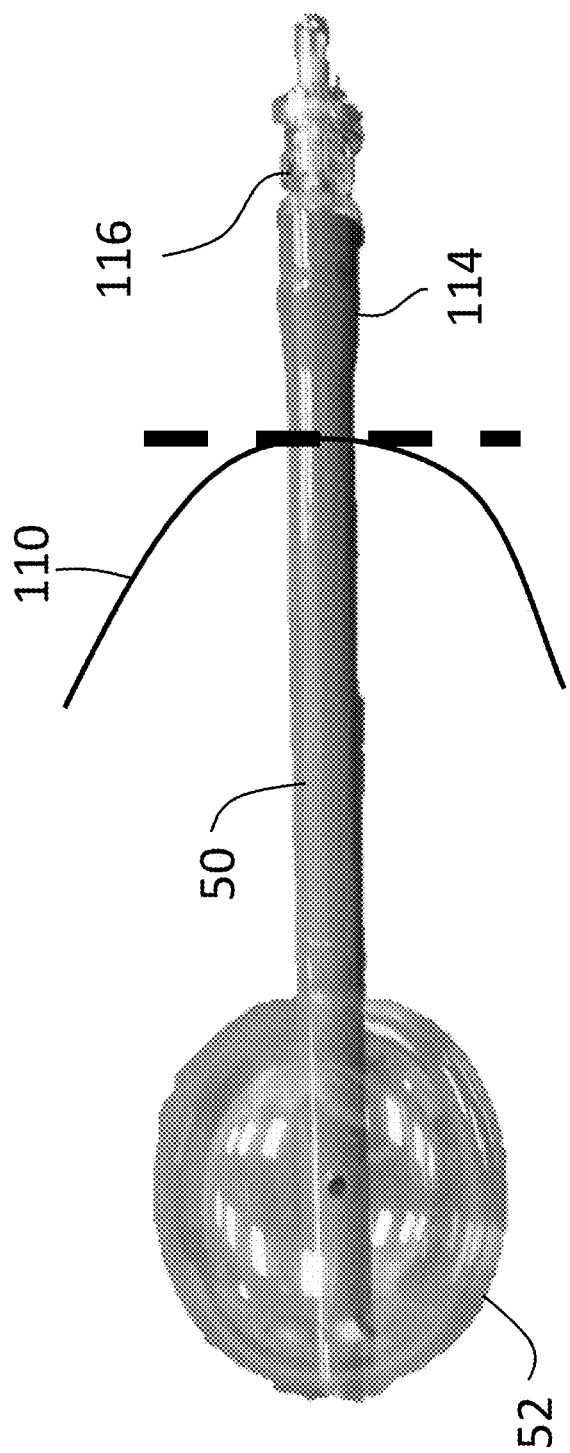
Figure 22:
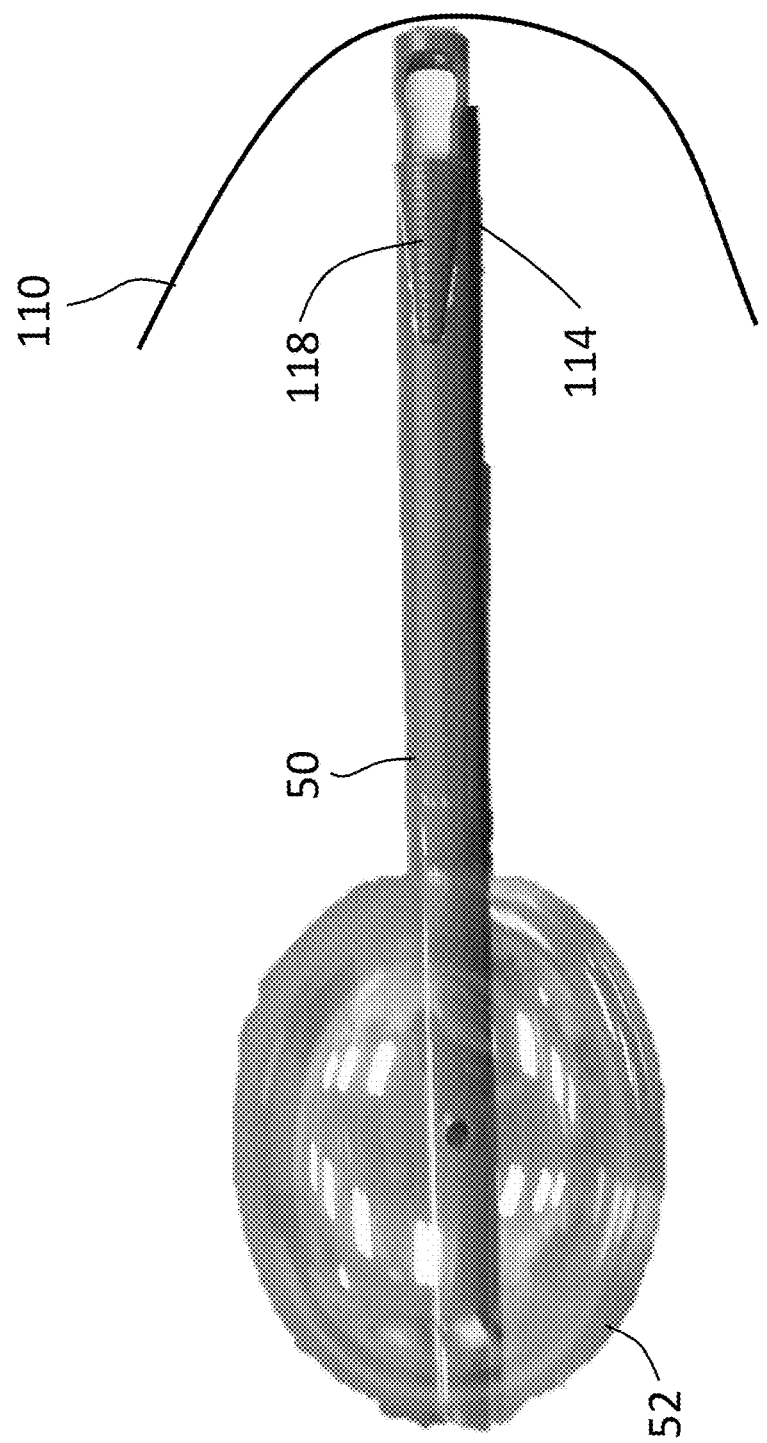

Referring now to FIGS. 19-23, a method is shown of performing the biopsy procedure. The method starts with the surgeon performing the biopsy from the breast 110 and removing the sample to form a space 112. The catheter 50 with the balloon 52 coupled to one end is inserted into the breast 110 (FIG. 19). The end 114 of the catheter 50 is external of the breast where a Luer lock 116 attaches to the syringe 102.

Using the syringe 102 (FIG. 20), the balloon is filled by the desired amount of fluid (e.g. saline). During the filling process, the valve 47 and the luer lock 116 reduce or eliminate backflow of fluid from the balloon 52. The syringe 102 is removed (FIG. 21) from the catheter 50 and the catheter 50 is cut using surgical scissors 208 (FIG. 24) just below the breast 110 outer layer. A catheter plug 118, such as a Model DYND12200H catheter plug made by Medline Industries, Inc. of Mundelein, Ill. for example, is inserted (FIG. 22) into the end 114 to seal the catheter 50 from leakage for the period of time the balloon 52 is inside the breast 110. In an embodiment, the plug 118 may include members that facilitate finding the catheter after the testing of the biopsy specimen is complete. In one embodiment, the plug 118 may include a ferrous material that may be found using a magnet. In another embodiment, the catheter 50 may include a loop or ring that may be used to remove the catheter 50 and balloon 52.

It should be appreciated that the ability to cut the catheter 50 while maintaining the integrity of the balloon 50 provides advantages in accommodating different breast sizes allowing the plug 118 to be positioned below the surface of the skin. Allowing the plug 118 to remain below the surface of the skin allows the incision to be closed while the biopsy specimen is being tested.

Figure 23:
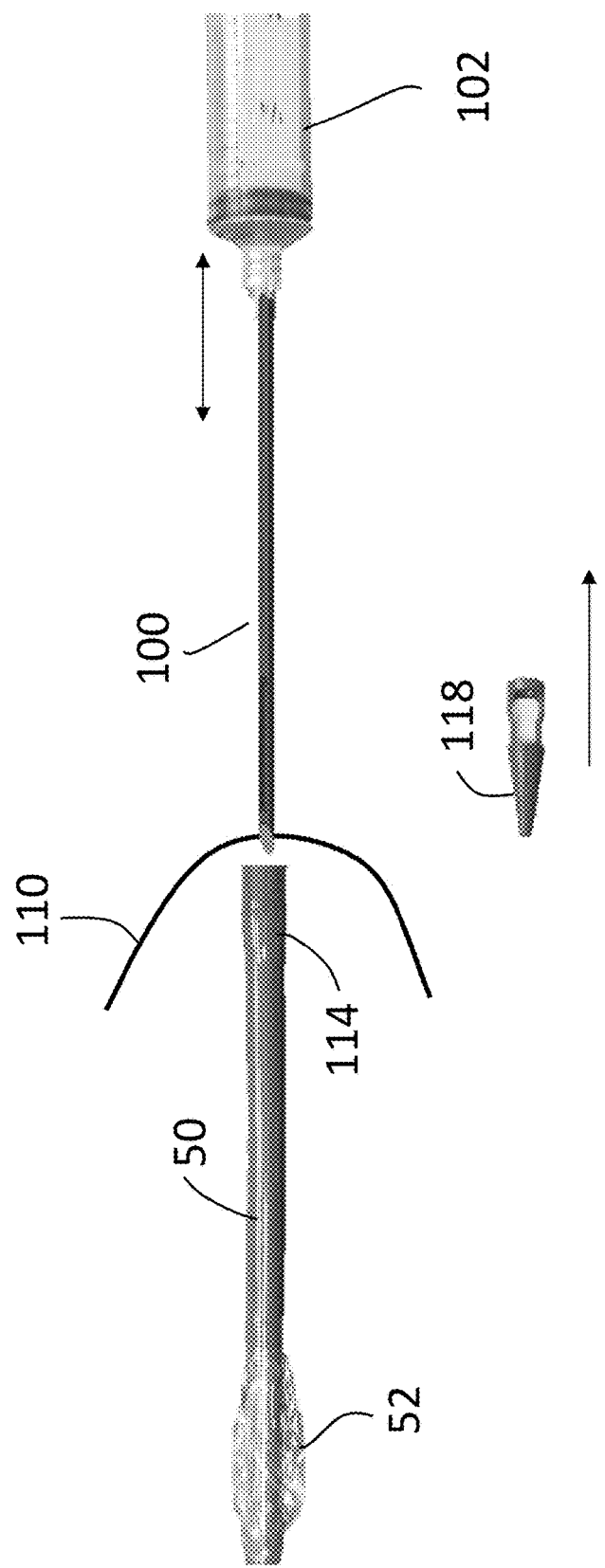

After a period of time, as typically determined by the surgeon, the incision is re-opened the catheter plug 118 is removed from the end 114 (FIG. 23). Due to the pressure in the balloon 52, the valve 47 remains in the closed position when the catheter plug 118 is removed. The surgeon attaches the draining device 100 to a syringe 102. The draining device 100 is inserted into the catheter 50 causing the end 104 to contact the end piece 57 of valve 47. The end 104 moves the valve 47 to open position by moving the head piece 59 (via the end piece 57 and rod 61). This allows the surgeon to suction the fluid from the balloon 52 using the syringe 102 via the opening 108 in draining device 100. In one embodiment, the draining device 100 is used without the syringe 102 to remove fluid from the balloon 52. Finally, forceps (not shown) are used to pull the deflated balloon 52 and catheter 50 from the breast 110. As discussed herein, the catheter 50 may include features, such as a ring or loop, that may be held and pulled by the surgeon to allow the catheter 50 and balloon 52 to be removed from the breast 110.

Figure 24:
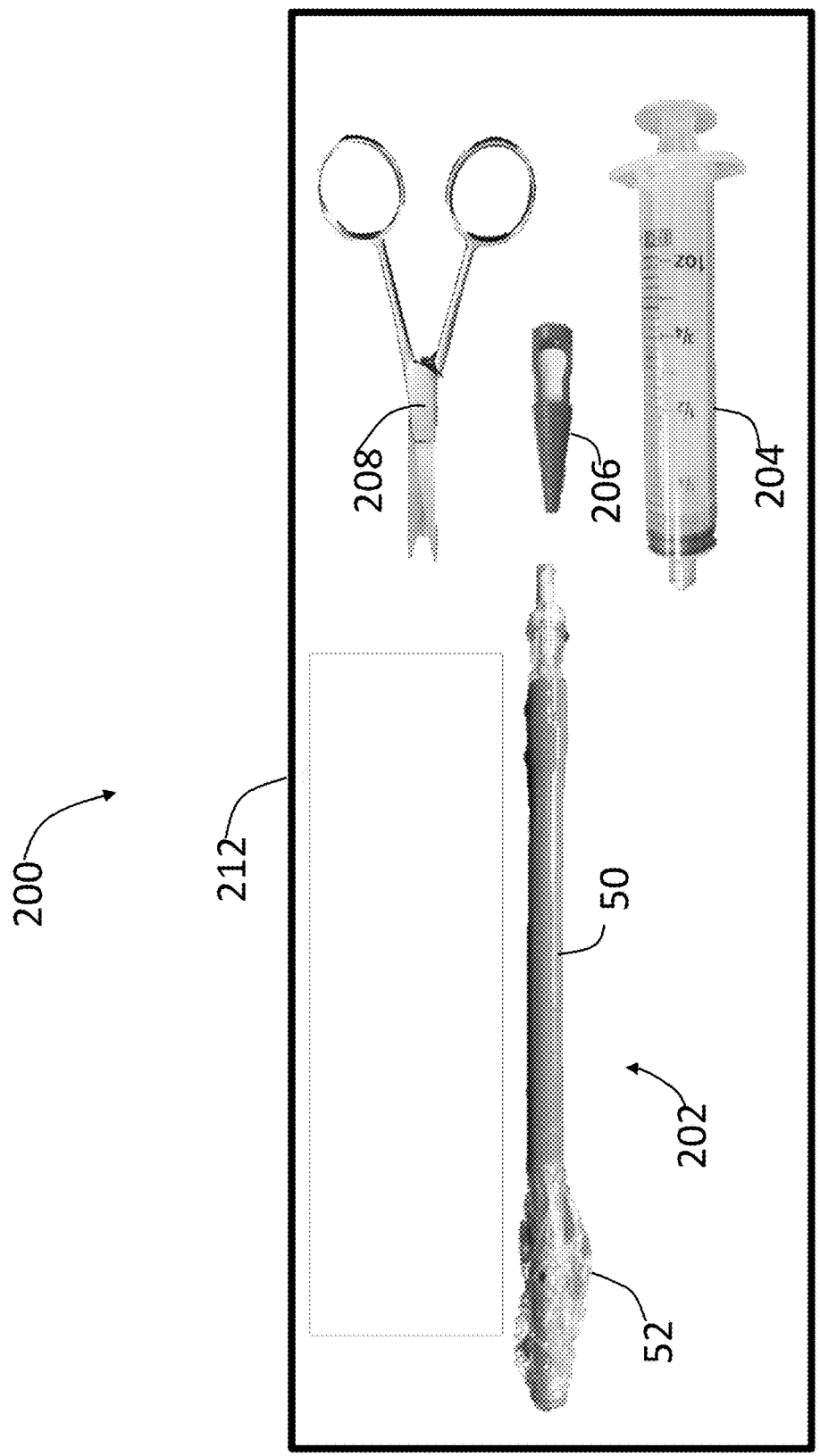
FIG. 24 illustrates a kit for performing a biopsy procedure, such as a percutaneous lumpectomy.

Referring now to FIG. 24, an embodiment is shown of a biopsy kit 200 for performing a percutaneous lumpectomy. The kit 200 includes a spacer device 202 having a catheter 50 with a balloon 52 disposed on a first end. The balloon 52 is fluidly coupled to a second end of the catheter 50. Coupled within the catheter 50 is an umbrella valve as described herein. In an embodiment, the second end may include a Luer lock device. In an embodiment, the kit 200 may further include a syringe 204 and a catheter plug 206. In still a further embodiment, the kit 200 may further include surgical scissors 208.

In further embodiments, the kit may also include sterile scissors, skin preparation solutions, a ruler sized to measure the incision tract, disposable needle holders, suture materials, lidocaine and sponges.

The individual components of the kit 200 may be contained in packaging 212. The packaging 212 for the kit 200 may be made of one or more of polymers, metals and or fiber materials according to methods known in the art.

It should be appreciated that while embodiments herein describe the use of the spacer device in conjunction with a percutaneous lumpectomy, this is for exemplary purposes and the claimed invention should not be so limited. The invention may also be used with internal radiotherapy, sealed source radiotherapy, curietherapy or endocurietherapy in the treatment of cervical, breast, prostate or skin cancer for example.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A cavity spacer device, the device comprising:
a catheter;
a self-sealing balloon member removably and fluidly coupled on one end of the catheter; and
an umbrella valve coupled to the catheter adjacent the balloon member, the umbrella valve having an end piece coupled to a head piece by a rod, the umbrella valve further includes a holder member slidably disposed on the rod, the holder member having a plurality of openings evenly spaced radially about the holder member, the end piece being sized to slide and engage the holder member and allow fluid flow into the balloon member in response to fluid flow from an end of the catheter opposite the balloon member and the head piece is sized to slide and engage the holder member and prevent fluid flow from the balloon member when fluid flow from the end of the catheter is stopped.

2. The cavity spacer device of claim 1, wherein the head piece is made from an elastomeric material.

3. The cavity spacer device of claim 1, wherein the plurality of openings are evenly spaced radially about the holder member.

4. The cavity spacer device of claim 1, wherein the plurality of openings are evenly spaced radially about the holder member.

5. A cavity spacer device the device comprising
a catheter;
a self-sealing balloon member removably and fluidly coupled on one end of the catheter;
an umbrella valve coupled to the catheter adjacent the balloon member, the umbrella valve being configured to allow fluid flow into the balloon member in response to fluid flow from an end of the catheter opposite the balloon member and prevent fluid flow from the balloon member when fluid flow from the end of the catheter is stopped;
an end piece;
a head piece coupled to the end piece;
a holder member operably coupled between the end piece and the head piece; and,
a draining device having a body with a closed end and an opposing open end, the body being sized and shaped to be received in the catheter, the body having a passageway extending from the open end to an opening, wherein draining device is configured to contact the end piece when inserted into the catheter and move the head piece from the closed position to the open position.

6. A biopsy kit for performing a percutaneous lumpectomy, the kit comprising:
a catheter plug;
a cavity spacer device having a catheter, a self-sealing balloon member removably and fluidly coupled on a first end of the catheter, and an umbrella valve coupled to the catheter adjacent the balloon member, the umbrella valve having an end piece coupled to a head piece by a rod, the umbrella valve further includes a holder member slidably disposed on the rod, the holder member having a plurality of openings evenly spaced radially about the holder member, the end piece being sized to slide and engage the holder member and allow fluid flow into the balloon member in response to fluid flow from a second end of the catheter opposite the first end and the head piece is sized to slide and engage the holder member and prevent fluid flow from the balloon member when fluid flow from the second end is stopped; and
a drainage device sized to fit within the catheter and couple to a syringe.

7. The biopsy kit of claim 6, further comprising the syringe configured to couple with the catheter and the drainage device.

8. The biopsy kit of claim 7, the second end configured to couple with the syringe and catheter plug.

9. The biopsy kit of claim 7, wherein the draining device includes a body with a closed end and an opposing open end, the body being sized and shaped to be received in the catheter, the body having a passageway extending from the open end to an opening.

10. The biopsy kit of claim 6, wherein the head piece is made from an elastomeric material.

11. A biopsy kit for performing a percutaneous lumpectomy, the kit comprising:
a catheter plug;
a cavity spacer device having a catheter, a self-sealing balloon member removably and fluidly coupled on a first end of the catheter, and an umbrella valve coupled to the catheter adjacent the balloon member, the umbrella valve having an end piece, a head piece coupled to the end piece and a holder member operably coupled between the end piece and the head piece, the umbrella valve being configured to fluid flow into the balloon member in response to fluid flow from a second end of the catheter opposite the first end and prevent fluid flow from the balloon member when fluid flow from the second end is stopped; and
a drainage device sized to fit within the catheter and couple to a syringe, the drainage device having a body with a closed end and an opposing open end, the body being sized and shaped to be received in the catheter, the body having a passageway extending from the open end to an opening, wherein draining device is configured to contact the end piece when inserted into the catheter and move the head piece from the closed position to the open position.

\* \* \* \* \*